United States Patent
Murakami

(10) Patent No.: US 6,821,421 B2
(45) Date of Patent: Nov. 23, 2004

(54) HEMODIALYZING UNIT FOR ADJUSTING DIALYTIC FLUID TO LOW FLOW RATE

(75) Inventor: Tomoaki Murakami, Shimomashiki-gun (JP)

(73) Assignee: JMS Co., Ltd., Hiroshima (JP)

( * ) Notice: Subject to any disclaimer, the term of this patent is extended or adjusted under 35 U.S.C. 154(b) by 182 days.

(21) Appl. No.: 10/196,316

(22) Filed: Jul. 16, 2002

(65) Prior Publication Data

US 2004/0011722 A1 Jan. 22, 2004

(51) Int. Cl.[7] .......................... B01D 61/28; B01D 61/32
(52) U.S. Cl. .................. 210/321.71; 210/97; 210/232; 210/254; 210/258
(58) Field of Search .................. 210/86, 87, 97, 210/143, 232, 254, 258, 321.65, 321.71

(56) References Cited

U.S. PATENT DOCUMENTS

| | | | | |
|---|---|---|---|---|
| 4,229,299 A | * | 10/1980 | Savitz et al. ................... 210/85 |
| 5,431,811 A | * | 7/1995 | Tusini et al. ................... 210/90 |
| 5,733,457 A | * | 3/1998 | Hovland et al. .............. 210/636 |
| 6,156,002 A | * | 12/2000 | Polaschegg et al. ........ 604/4.01 |
| 6,331,252 B1 | * | 12/2001 | El Sayyid et al. ........... 210/646 |
| 2004/0020852 A1 | * | 2/2004 | Olsson ......................... 210/646 |

FOREIGN PATENT DOCUMENTS

| JP | 6-36826 | 9/1994 |
|---|---|---|
| JP | 3052751 | 7/1998 |
| JP | 2000-237305 | 9/2000 |

* cited by examiner

*Primary Examiner*—John Kim
(74) *Attorney, Agent, or Firm*—Merchant & Gould P.C.

(57) ABSTRACT

A hemodialyzing unit includes a dialytic fluid supply line for feeding a dialytic fluid from a dialytic fluid supply/discharge unit to a dialyzer, a dialytic fluid discharge line for feeding a dialytic fluid discharged from the dialyzer to the dialytic fluid supply/discharge unit, and a bypass line for connecting both lines at an intermediate portion of each. A flow rate adjusting member is provided to a downstream supply line between a coupling portion for coupling the dialytic fluid supply line to the bypass line and the dialyzer. A wider range of treatments such as CHD (or CHDF), SHD (or SHDF), and HD (or HDF) can be conducted without employing a device for the exclusive use of the CHD or CHDF.

15 Claims, 6 Drawing Sheets

HEMODIALYZING UNIT FOR ADJUSTING DIALYTIC FLUID TO LOW FLOW RATE

FIELD OF THE INVENTION

The present invention relates to a hemodialyzing unit that removes waste products on the blood from a patient suffering from renal insufficiency or the like, employing a hemodialysis membrane, and more particularly, to the hemodialyzing unit that is applied to a case where dialysis is difficult to perform at a general flow rate of dialytic fluid, and a dialytic fluid circuit for the same.

BACKGROUND OF THE INVENTION

When hemodialysis is conducted employing an artificial dialyzer, a blood pump and a dialytic fluid pump are controlled in a hemodialyzing unit as follows. The blood pump is controlled so that the flow rate of blood circulating in a blood circuit is constant. The dialytic fluid pump is controlled so that the flow rate of dialytic fluid in contact with the blood through a hemodialysis membrane is constant similarly (by a single-path method). According to the hemodialysis, substances are transferred between the dialytic fluid and the blood, thereby removing moisture or waste products in the blood. The removed quantity is closely related to the blood flow rate and the flow rate of dialytic fluid. According to the general hemodialysis treatment (hemodialyzing unit), the flow rate of dialytic fluid is 500 ml/min, and can be decreased so far as to reach a level of 300 ml/min.

However, the general hemodialysis cannot be applied to types of patients and cases such as a patient who tends to be in disequilibrium syndrome, a case of a renal disease having a complication of a circulatory system or a case of a multiple organ failure. For these patients and cases, the application of a Continuous Hemo Dialysis (CHD), a Continuous Hemo Filtration (CHF), and a Continuous Hemo Dia-Filtration (CHDF) has been studied and exhibits some effects. The CHD and CHDF are characterized by continuously and slowly conducting water removal or fluid supply. However, according to these methods, it is difficult to adjust the flow rate in a low flow rate range in the general hemodialyzing unit or a dialytic fluid supply unit. Therefore, the CHD or CHDF requires a device for the exclusive use, and further, supplemental fluid for a filtering-type artificial kidney to be given.

SUMMARY OF THE INVENTION

Therefore, with the foregoing in mind, it is an object of the present invention to provide a hemodialyzing unit that can be used at a low flow rate of dialytic fluid, by which a wide range of treatments of the CHD (or CHDF), SHD (or SHDF), and HD (or HDF) can be conducted without employing a special device for the exclusive use required for conducting the CHD or CHDF. Moreover, it is an object of the present invention to provide a hemodialyzing unit for conducting these treatments at low cost, and a dialytic fluid circuit for the same.

It should be noted that the SHD designates Slow Hemo Dialysis and the SHDF designates Slow Hemo Dia-Filtration in the specification, which are conducted at a low flow rate of dialytic fluid. More specifically, the SHD and the SHDF refer to the dialysis in which a dialytic fluid has a decreased flow rate, so as to be flowed slowly, whereby the water removal or the substance transfer is performed slowly.

The above-mentioned treatment is applied to a linking (intermediate) treatment for a patient having serious renal insufficiency when the treatment is shifted from the CHD (or CHDF) to the HD (or HDF). According to the treatment, the flow rate of dialytic fluid is in a range of about 10 to 250 ml/min (not exceeding 300 ml/min to be the lowest flow rate for the general dialyzing unit). One dialysis period (treatment period) is about 4 or 5 hours to 8 hours, similarly to the case of the general dialysis. It does not take as long as the case of the CHD, which takes 12 to 24 hours.

It is another object of the present invention to provide a hemodialyzing unit that can be applied to both cases of the general hemodialysis and the hemodialysis at a low flow rate of dialytic fluid. To be specific, the present invention aims to provide a hemodialyzing unit that can be used for the general hemodialysis in a usual mode, and, if required, can be used for conducting a wide range of treatments, such as CHD (or CHDF), SHD (or SHDF), and HD (or HDF) by a minor change in the device configuration.

The hemodialyzing unit of the present invention includes a dialytic fluid supply line for feeding a dialytic fluid from a dialytic fluid supply/discharge unit to a dialyzer, a dialytic fluid discharge line for feeding a dialytic fluid discharged from the dialyzer to the dialytic fluid supply/discharge unit, and a bypass line for connecting both the lines at the respective intermediate portions. Accordingly, the dialytic fluid supply line includes an upstream supply line extending from the dialytic fluid supply/discharge unit to a coupling portion to the bypass line and a downstream supply line extending from the coupling portion to the bypass line to the dialyzer. Further, the dialytic fluid discharge line includes an upstream discharge line extending from the dialyzer to the coupling portion to the bypass line and a downstream discharge line extending from the coupling portion to the bypass line to the dialytic fluid supply/discharge unit. The downstream supply line is provided with a flow rate adjusting member.

As described above, the downstream supply line is provided with the flow rate adjusting member, thereby controlling the flow rate of the dialytic fluid flowing into the dialyzer. Since the general dialytic fluid supply/discharge unit cannot adjust the dialytic fluid to be fed to the dialytic fluid supply line at a low flow rate, the normal flow rate of dialytic fluid flows into the upstream supply line. In contrast, the downstream supply line is additionally provided with the flow rate adjusting member, whereby the flow rate of dialytic fluid is controlled to be low, and consequently, the dialytic fluid can be fed to the dialyzer at a low flow rate. The dialytic fluid that passes through the upstream supply line, not to be fed to the dialyzer, becomes a redundant dialytic fluid. The redundant dialytic fluid passes through the bypass line, and then the downstream discharge line, to be discharged from the dialytic fluid supply/discharge unit.

Any flow rate adjusting member may be used as long as it suitably adjusts the flow rate of dialytic fluid of the downstream supply line, preferably having a simple structure. For instance, the flow rate adjusting member can be composed of a dialytic fluid feed pump, or a dialytic fluid feed pump and a pump tube attached thereto. Moreover, it is preferable that the flow rate adjusting member can adjust the flow rate of dialytic fluid in a lower flow rate range than the dialytic fluid supply/discharge unit. There is no particular limit to the dialytic fluid feed pump; however, in general, a roller pump or a peristaltic pump, or the like is employed, for instance.

Moreover, in the hemodialyzing unit having the above-mentioned configuration, it is more preferable to control the dialytic fluid feeding rate through the upstream supply line to be larger than that through the downstream supply line.

Therefore, it is preferable for the hemodialyzing unit of the present invention to employ a dialytic fluid feed pump capable of adjusting the flow rate to be 150 ml/hr. In view of the upper limit of the flow rate of dialytic fluid, it is preferable to adjust the flow rate of dialytic fluid in a range of the lowest dialytic fluid feeding rate of 150 ml/hr to the highest dialytic fluid feeding rate of 30,000 ml/hr. If it is desired to accurately control the dialytic fluid feeding rate in a low flow rate range, it is preferable to use the pump having a controllable range in the lowest flow rate of dialytic fluid of 150 ml/hr to the highest flow rate of dialytic fluid of 9,000 ml/hr. Moreover, the use of the dialytic fluid feed pump, to which pump tubes having different diameters can be attached, allows the flow rate setting range to be varied by exchanging the pump tube. The general dialysis can be conducted sufficiently at the lowest flow rate of dialytic fluid of 500 ml/min. Accordingly, in the usual case, a pump tube suitable for the set flow rate is attached to the dialytic fluid feed pump, and in the case where the flow rate is required to be set lower, the pump tube having a smaller diameter may be employed.

Further, in the hemodialyzing unit having the above-described configuration, it is preferable to provide at least one open/close member to the upstream supply line and the downstream discharge line, respectively, thereby ensuring safety of the patient To be specific, when the dialytic fluid feeding system or the dialytic fluid discharge system of the dialytic fluid supply/discharge unit falls into an abnormal condition, the respective open/close members provided on both the lines are closed. Therefore, the connection to the dialytic fluid supply/discharge unit is cut off so as to form a recirculating loop defined by the downstream supply line, the upstream discharge line, and the bypass line.

Further, it is preferable to provide an open/close member such as a solenoid valve or the like to the bypass line. Therefore, the normal channel of the dialytic fluid circuit (defined by the dialytic fluid supply/discharge unit, the dialytic fluid supply line, the dialyzer, the dialytic fluid discharge line, and the dialytic fluid supply/discharge unit) can be selected without using a closing member such as a forceps, or a mode in which the dialytic fluid flows at a low flow rate can be selected. Moreover, when the open/close member is provided to the bypass line, the line can be cleaned/disinfected. When the solenoid valve is employed as the open/close member, the solenoid valve is incorporated in the dialyzing unit so as to switch automatically between the dialysis and the cleaning. According to the use state, a hand-operated valve may be employed instead of the solenoid valve. As described above, the circuit for the dialytic fluid at a low flow rate previously is incorporated in the dialyzing unit, whereby the switching among the HD, SHD, CHD, and the like can be simplified. Therefore, the emergency case can be managed with ease.

When a sodium injecting unit is provided to the dialytic fluid supply/discharge unit, dialysis of high sodium at a low flow rate can be realized, which was not easily conducted by the device for the exclusive use of the CHD or CHDF.

The following configuration allows a hemodialyzing unit to conduct the general hemodialysis in a usual mode, and, only when required, to set the dialytic fluid at a low flow rate. To be specific, the hemodialyzing unit having any of the above-described configurations is configured so that complementary connector pairs are provided to the respective lines of the upstream supply line, the downstream discharge line, the downstream supply line extending from the attachment portion of the flow rate adjusting member to the dialyzer and the upstream discharge line, respectively, in order to disconnect/reconnect the respective lines at each complementary connector pair.

For instance, the upstream supply line extending from the first open/close member provided at the upstream supply line to the dialytic fluid supply/discharge unit is provided with a first complementary connector so as to be disconnected/reconnected. The downstream discharge line extending from the second open/close member provided at the downstream discharge line to the dialytic fluid supply/discharge unit is provided with a second complementary connector so as to be disconnected/reconnected. The downstream supply line extending from the attachment portion to the flow rate adjusting member to the dialyzer is provided with a third complementary connector so as to be disconnected/reconnected. The upstream discharge line is provided with a fourth complementary connector so as to be disconnected/reconnected.

The hemodialyzing unit includes two devices and circuit configurations. One device body or circuit body includes the dialytic fluid supply line for feeding the dialytic fluid from the dialytic fluid supply/discharge unit to the dialyzer, and the dialytic fluid discharge line for feeding the dialytic fluid discharged from the dialyzer to the dialytic fluid supply/discharge unit. The dialytic fluid supply line includes a first detachable portion composed of a complementary connector pair at the intermediate portion so as to be disconnected/reconnected by detachment of the complementary connector pair at the first detachable portion. The dialytic fluid discharge line includes a second detachable portion composed of a complementary connector pair at the intermediate portion so as to be disconnected/reconnected by detachment of the complementary connector pair at the second detachable portion.

Further, the other unit or circuit includes a dialytic fluid supply extension-line, a dialytic fluid discharge extension-line, and a bypass line for connecting both the extension lines at each intermediate portion. Complementary connectors are disposed at both the ends of the dialytic fluid supply extension-line so as to be connected to each of the disconnected complementary connectors of the first detachable portion in the above configuration. Complementary connectors are disposed at both the ends of the dialytic fluid discharge extension-line so as to be connected to each of the disconnected complementary connectors of the second detachable portion. A flow rate adjusting member is provided between the coupling portion to the bypass line of the dialytic fluid supply extension-line and one end of the dialytic fluid supply extension-line. Thus, a unit can be configured to serve as an incorporation dialytic fluid circuit.

In the case where the general hemodialysis is conducted in those configurations, a hemodialyzing unit including the first detachable portion and the second detachable portion is used while the respective detachable portions are connected. In this case, the hemodialyzing unit configured as described above can be used in the same manner as the general hemodialyzing unit.

When the dialytic fluid needs to flow into the dialyzer at a low flow rate, the respective complementary connectors of the first and second detachable portions are disconnected. Then, the dialytic fluid supply extension-line is inserted into the dialytic fluid supply line, and the dialytic fluid discharge extension-line is inserted into the dialytic fluid discharge line. Thus, a hemodialyzing unit, in which the incorporation dialytic fluid circuit is inserted, can be formed. In this state, the flow rate adjusting member provided at the dialytic fluid supply line reduces the flow rate of the dialytic fluid flowing into the dialyzer (i.e., the flow rate of the dialytic fluid passing through the downstream supply line). However, there is no change in the flow rate of the dialytic fluid flowing from the dialytic fluid supply/discharge unit to the dialytic fluid supply line. Therefore, the redundant dialytic fluid passes through the bypass line, and then, through the downstream discharge line, to be discharged from the dialytic fluid supply/discharge unit. According to the above-described system, only when required, the flow rate of the dialytic fluid passing through the dialyzer can be adjusted to be low, simply and exactly.

The hemodialyzing unit configured as described above may be configured including a flow rate adjusting line, a blood circuit connecting line, and a control unit as follows. The flow rate adjusting line arranged in parallel to the dialytic fluid discharge line includes a first flow rate adjusting unit for adjusting the flow rate of dialytic fluid. The blood circuit connecting line including a second flow rate adjusting unit for adjusting the flow rate of dialytic fluid is provided so as to connect the bypass line to the blood circuit. The control unit for controlling the first and second flow rate adjusting units is provided so that the flow rate of dialytic fluid through the flow rate adjusting line is equal to that through the blood circuit connecting line. According to the above configuration, an on-line HDF (Hemo Dia-Filtration) can be conducted at a low flow rate of dialytic fluid.

DETAILED DESCRIPTION OF THE INVENTION

First Embodiment

Figure 1:
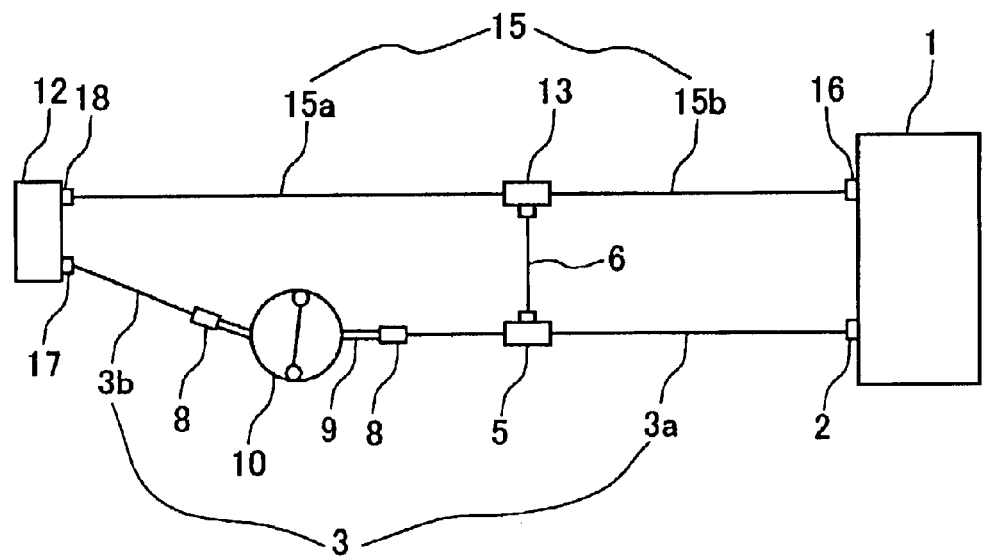
FIG. 1 is a schematic view illustrating a configuration of a hemodialyzing unit according to a first embodiment of the present invention.

FIG. 1 is a schematic view illustrating a configuration of a hemodialyzing unit according to a first embodiment of the present invention. A dialytic fluid circuit is configured so as to feed a dialytic fluid from a dialytic fluid supply/discharge unit 1 to a hemodialyzer 12, and to feed a dialytic fluid discharged from the dialyzer 12 to the dialytic fluid supply/discharge unit 1. The dialytic fluid supply/discharge unit 1 is controlled so that the flow rate of the dialytic fluid fed to a dialytic fluid supply line 3 is equal to the flow rate of the dialytic fluid fed from a dialytic fluid discharge line 15 by a closed-type volume control method.

The dialytic fluid supply/discharge unit 1 is coupled to the dialytic fluid supply line 3 and the dialytic fluid discharge line 15 via a supply line coupler 2 and a discharge line coupler 16, respectively. Further, the hemodialyzer 12 is coupled to the dialytic fluid supply line 3 and the dialytic fluid discharge line 15 via an inflow port 17 and an outflow port 18, respectively. The dialytic fluid supply line 3 and the dialytic fluid discharge line 15 are coupled to a bypass line 6 at a supply line coupling portion 5 and a discharge line coupling portion 13, which are placed at an intermediate portion of the respective lines. The both lines 3 and 15 are connected to each other by the bypass line 6.

Here, for simplifying the explanation, each section is defined as follows. A section from the supply line coupler 2 to the supply line coupling portion 5 is defined as an upstream supply line 3a. A section from the supply line coupling portion 5 to the inflow port 17 is defined as a downstream supply line 3b. A section from the outflow port 18 to the discharge line coupling portion 13 is defined as an upstream discharge line 15a. A section from the discharge line coupling portion 13 to the discharge line coupler 16 is defined as a downstream discharge line 15b.

At an appropriate portion of the downstream supply line 3b, a pump tube 9 is inserted via a pump tube coupler 8. The pump tube 9 is attached to a roller (dialytic fluid feeding) pump 10. The roller pump 10 is used for adjusting the flow rate of dialytic fluid passing through the downstream supply line 3b to a low flow rate. The purpose of inserting the pump tube 9 to the pump by the pump tube coupler 8 is to facilitate the exchange of the pump tube 9. Therefore, in the case where the pump tube 9 is worn out or its diameter needs to be varied, the exchange of the pump tube 9 can be simplified.

In the present embodiment, the dialytic fluid fed from the dialytic fluid supply/discharge unit 1 partially flows into the dialyzer 12 by the roller pump 10. The dialytic fluid that passes through the upstream supply line 3a, but is not fed to the dialyzer 12 becomes a redundant dialytic fluid. The redundant dialytic fluid passes through the bypass line 6, the downstream discharge line 15b, and then the dialytic fluid supply/discharge unit 1, to be discharged out of the dialytic fluid circuit. According to the hemodialyzing unit having a simple configuration as described above, the dialytic fluid flowing into the dialyzer 12 can be adjusted at a low flow rate, so as to be applied to a wide range of treatments, such as CHD (or CHDF), SHD (or SHDF) and HD (or HDF).

Figure 6:
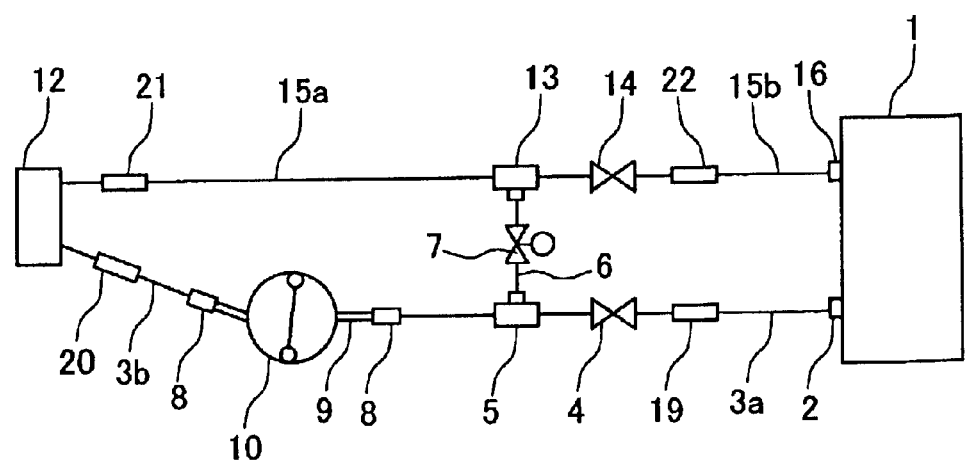
FIG. 6 is a schematic view illustrating a configuration of a hemodialyzing unit according to a fourth embodiment of the present invention.

When the hemodialyzing unit according to the present embodiment is used for the general hemodialysis, the pump tube 9 is disconnected from the roller pump 10, and further the bypass line 6 is closed at an appropriate portion by a forceps or the like. Otherwise, as shown in FIG. 6, an open/close member such as a solenoid valve 7 may be provided to the bypass line 6 in advance so that a channel is opened when the CHD (or CHDF) or the SHD (or SHDF) is conducted, while the channel is closed when the general dialysis is conducted.

According to the dialytic fluid supply/discharge unit 1, the dialytic fluid feeding rate can be controlled in a range from 18,000 to 30,000 ml/hr (300 to 500 ml/min) at most. Therefore, it is difficult to feed a dialytic fluid at a low flow rate applicable to the CHD (or CHDF) or the SHD (or SHDF). In contrast, the dialytic fluid feeding rate controlled by the dialytic fluid feed pump 10 is in a range of 150 to 18,000 ml/hr (2.5 to 300 ml/min). Therefore, the dialytic fluid can be adjusted to be fed at a low flow rate applicable to the CHD (or CHDF) or the SHD (or SHDF). Since the general dialysis can be conducted sufficiently at a dialytic fluid feeding rate of 500 ml/hr at the lowest, the pump tube 9 having a diameter suitable for the dialytic fluid feeding rate is employed. When a much lower flow rate is desired, a pump tube 9 having a much smaller diameter is adopted, thereby realizing the dialytic fluid feeding rate of 150 ml/hr.

Second Embodiment

Figure 2:
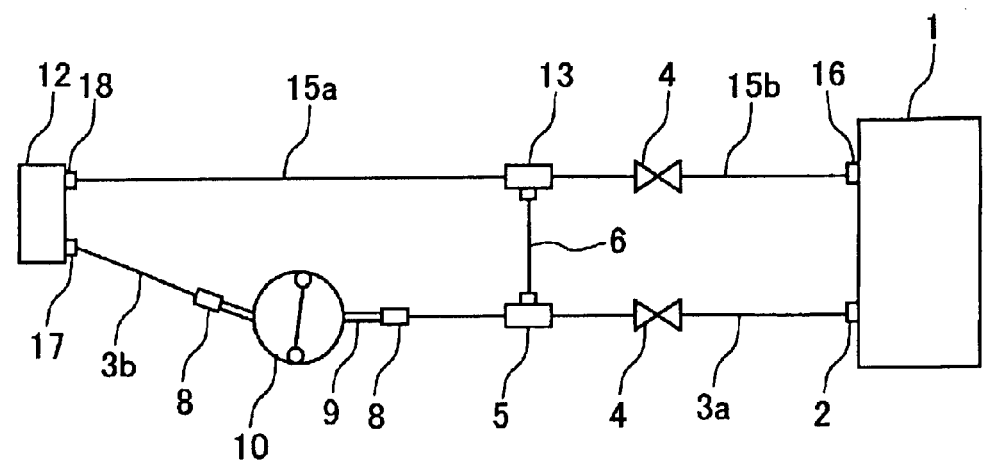
FIG. 2 is a schematic view illustrating a configuration of a hemodialyzing unit according to a second embodiment of the present invention.

FIG. 2 is a schematic view illustrating a configuration of the hemodialyzing unit according to a second embodiment. According to the present embodiment, open/close members (valves) 4 and 14 are provided in the upstream supply line 3a and the downstream discharge line 15b, respectively.

In this configuration, when the dialytic fluid feeding function of the dialytic fluid supply/discharge unit 1 falls into an abnormal condition, the both valves 4, 14 are closed so that the upstream supply line 3a and the downstream discharge line 15b can be closed temporarily. Under this state, a recirculating loop can be formed consisting of the downstream supply line 3b, the dialyzer 12, the upstream discharge line 15a, the bypass line 6, and the downstream supply line 3b. Therefore, the safety of the patient can be secured.

Third Embodiment

Figure 3:
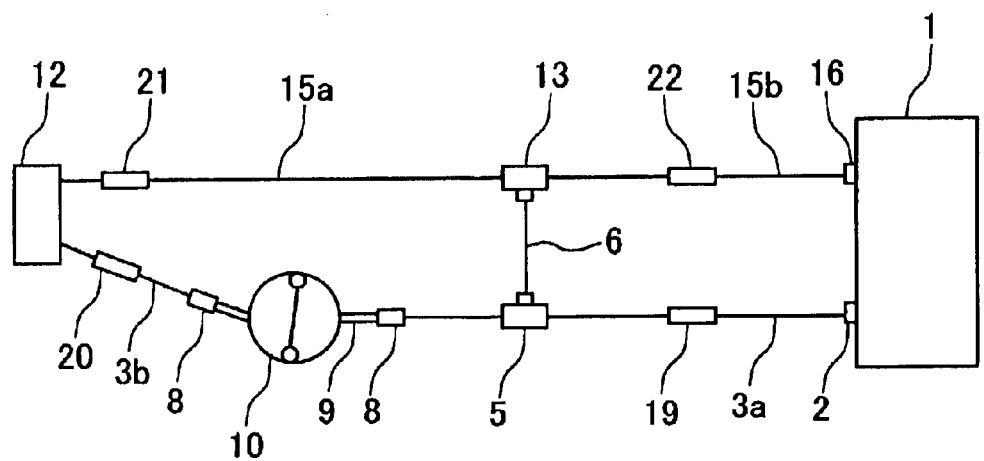
FIG. 3 is a schematic view illustrating a configuration of a hemodialyzing unit according to a third embodiment of the present invention.

FIG. 3 is a schematic view illustrating a configuration of the hemodialyzing unit according to a third embodiment. According to this embodiment, complementary connector pairs 19, 20, 21 and 22 are provided to the upstream supply line 3a, the downstream supply line 3b, the upstream discharge line 15a, and the downstream discharge line 15b, respectively. The complementary connector pair means a combination of connectors that can be freely disconnected/connected, such as a male connector and a female connector. As the connector, a lock-type connector that can be screwed or a lure-type connector that can be engaged without locking may be used.

Figure 4:
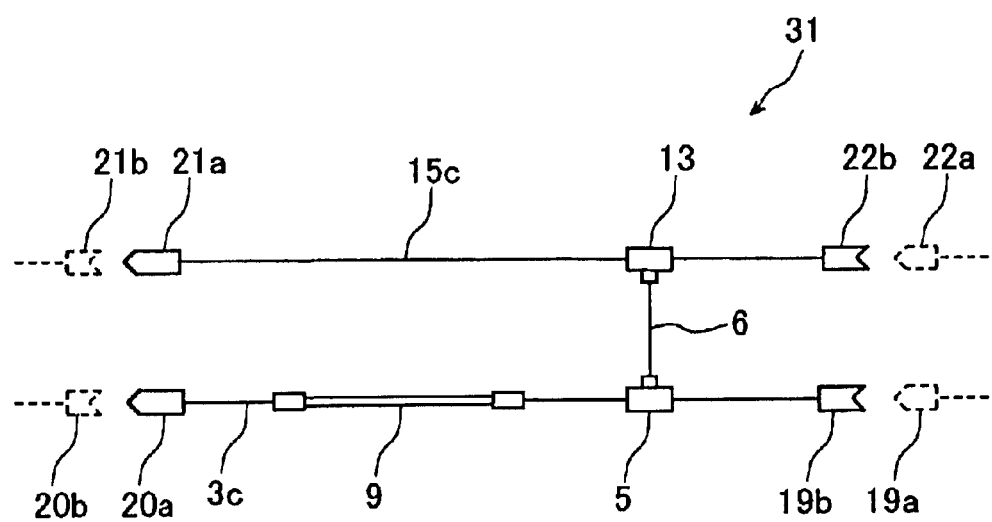
FIG. 4 is a schematic view illustrating an incorporation unit (line) constituting the hemodialyzing unit according to the third embodiment of the present invention.

The lines are divided by the complementary connector pairs 19, 20, 21 and 22, thereby forming, as shown in FIG. 4, an H-shaped incorporation line 31 including the bypass line 6 and the pump tube 9. The incorporation line 31 includes a dialytic fluid supply extension-line 3c provided with complementary connectors 19b and 20a at the both ends, a dialytic fluid discharge extension-line 15c provided with complementary connectors 21a and 21b at the both ends, and the bypass line 6 for connecting both the extension lines. The pump tube 9 is provided between the complementary connector 20a and the coupling portion 5 for coupling the dialytic fluid supply extension-line 3c to the bypass line 6.

If a female type connector is used as a complementary connector 19b attached to the end of the incorporation line 31 on the side of the upstream supply line, a male type connector should be used as a complementary connector 20a placed on the side of the downstream supply line. In contrast, if the complementary connector 19b is a male type connector, the complementary connector 20a should be a female type connector. That is, those connectors are designed to have a complementary relation.

As described above, it is made easy to change the circuit or unit so as to be used for general hemodialysis by providing the complementary connector pairs to each of the four lines. In such a case, first, the complementary connector pairs 19, 20, 21 and 22 are disconnected, and then the incorporation line 31 is removed.

Figure 5:
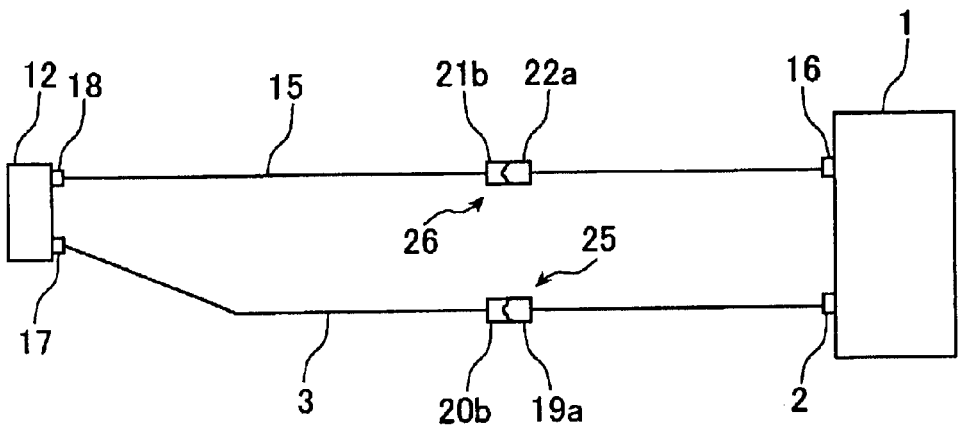
FIG. 5 is a schematic view illustrating another structure of the hemodialyzing unit according to the third embodiment of the present invention.

Then, the complementary connector 19a (male type) at a disconnected end of the upstream supply line 3a is connected to the complementary connector 20b (female type) at a disconnected end of the downstream supply line 3b. Moreover, the complementary connector 21b (female type) at the disconnected end of the upstream discharge line 15a is connected to the complementary connector 22a (male type) at the disconnected end of the downstream discharge line 15b. The dialytic fluid circuit formed as described above is shown in FIG. 5. The dialytic fluid circuit shown in FIG. 5 is similar to the generally used dialytic fluid circuit. However, the dialytic fluid circuit has a feature that the dialytic fluid supply line 3 includes a first detachable portion 25 composed of the complementary connector pair (19a and 20b), and the dialytic fluid discharge line 15 includes a second detachable portion 26 composed of the complementary connector pair (21b and 22a).

In the case where the CHD or the like is not conducted usually, but the general hemodialysis is conducted mostly, it may be accepted to adopt the configuration shown in FIG. 5 instead of forming the circuit or unit in FIG. 1 or 3, and prepare the incorporation circuit or (incorporation) unit in FIG. 4 for use when required. The configuration in FIG. 5 allows the general hemodialysis to be conducted without closing the bypass line, or the like.

In the case where it is used for the dialysis at a low flow rate of dialytic fluid, these complementary connector pairs are disconnected. Consequently, the disconnected ends having the complementary connectors 19a and 20b, respectively are formed on the dialytic fluid supply line 3, and the disconnected ends having the complementary connectors 21b and 22a, respectively are formed in the dialytic fluid discharge line 15. Subsequently, the incorporation line 31 in FIG. 4 is inserted between the disconnected ends formed in the respective lines, so that the respective pairs of the complementary connectors 19a and 19b, 20a and 20b, 21a and 21b, and 22a and 22b are connected to each other, respectively.

The incorporation line 31 is incorporated to the disconnected ends, and the pump tube 9 is attached to the dialytic fluid feed pump 10, thereby forming the unit for adjusting the dialytic fluid to a low flow rate as shown in FIG. 3. Therefore, the unit thus obtained can be applied to the CHD (or CHDF) easily and surely.

Fourth Embodiment

FIG. 6 is a schematic view illustrating a configuration of the hemodialyzing unit according to a fourth embodiment. In this embodiment, similarly to a second embodiment, the valves 4 and 14 are provided for the upstream supply line 3a and the downstream discharge line 15b, respectively.

Moreover, the upstream supply line 3a is provided with the complementary connector pair 19 on the upstream of the valve 4 (between the supply line coupler 2 and the valve 4). The downstream discharge line 15b is provided with the complementary connector pair 22 on the downstream of the valve 14 (between the valve 14 and the discharge line coupler 16). The downstream supply line 3b and the upstream discharge line 15a are provided with the complementary connector pairs 20 and 21, respectively. The open/close member such as a solenoid valve 7 is provided for the bypass line 6.

In the case where the solenoid valve 7 is employed as the open/close member, it can be incorporated into the dialyzing unit, and can switch automatically an operation between the dialysis and the cleaning. According to the use requirements, a hand-operated valve may be employed instead of the solenoid valve.

Fifth Embodiment

According to the following configuration of a fifth embodiment, an on-line CHDF at a low flow rate of dialytic fluid can be conducted.

For instance, in the hemodialyzing unit configured as described above, a flow rate adjusting line is formed in parallel to the dialytic fluid discharge line. The flow rate adjusting line is provided with a first flow rate adjusting unit for adjusting the dialytic fluid feeding rate of the line. Moreover, a blood circuit connecting line for connecting the bypass line and the blood circuit is formed. The blood circuit connecting line is provided with a second flow rate adjusting unit for adjusting the dialytic fluid feeding rate of the line. Moreover, a control unit is provided so as to control the dialytic fluid feeding rate through the flow rate adjusting line to be equal to that through the blood circuit connecting line. The control unit is configured to employ a weight balance control method or a volume control method so as to control the dialytic fluid feeding rate through the flow rate adjusting line to be equal to that through the blood circuit connecting line.

Figure 7:
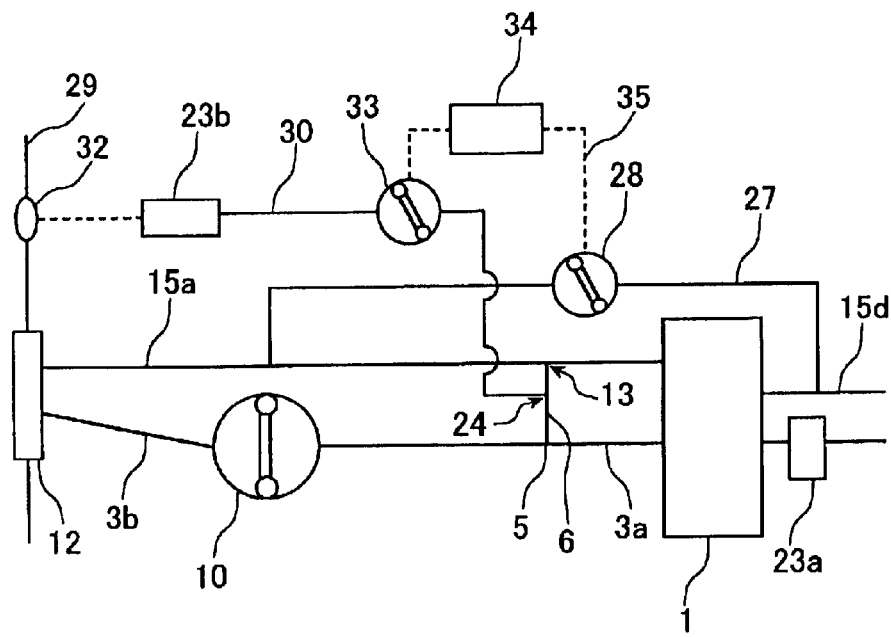
FIG. 7 is a schematic view illustrating a configuration of a hemodialyzing unit according to a fifth embodiment of the present invention.

The above configuration will be described in more detail with reference to FIG. 7. In FIG. 7, a system including the dialytic fluid supply/discharge unit 1, the bypass line 6, the roller pump 10, and the hemodialyzer 12 is configured similarly to the hemodialyzing unit in FIG. 1. In addition, a flow rate adjusting line 27 for removing water is formed in parallel to the dialytic fluid discharge line 15a. The flow rate adjusting line 27 is branched from the downstream discharge line 15a, to reach the discharge line 15d that is not placed within the system. A water removing pump 28 is attached to the flow rate adjusting line 27 as the first flow rate adjusting unit. Moreover, a blood circuit connecting line 30 for connecting the bypass line 6 to a blood circuit 29 is formed.

The blood circuit connecting line 30 has one end connected to an intermediate branch part 24 of the bypass line 6, and the other end connected to a chamber 32 of the blood circuit. A fluid supply pump 33 is attached to the blood circuit connecting line 30 as the second flow rate adjusting unit. Moreover, a linking control unit 34 is provided, to be connected to the water removing pump 28 and the fluid supply pump 33 via a controlling line 35. The linking control unit 34 controls the water removing pump 28 and the fluid supply pump 33 so that the dialytic fluid feeding rate becomes equal therebetween. Therefore, the quantity of fluid removed from the patient through the dialyzer 12 can be supplied to the blood circuit.

Further, if the unit according to the embodiment is expected to be employed as an on-line CHDF, it is preferable to provide an endotoxin (ET) cut filter 23a to a line for supplying a dialytic fluid to the dialytic fluid supply/discharge unit 1 Moreover, it is preferable to provide the ET cut filter 23b in the vicinity of the coupling portion between the blood circuit connecting line 30 and the blood circuit, and further it is preferable to examine the endotoxin value and confirm the safety for conducting the on-line CHDF.

Figure 8:
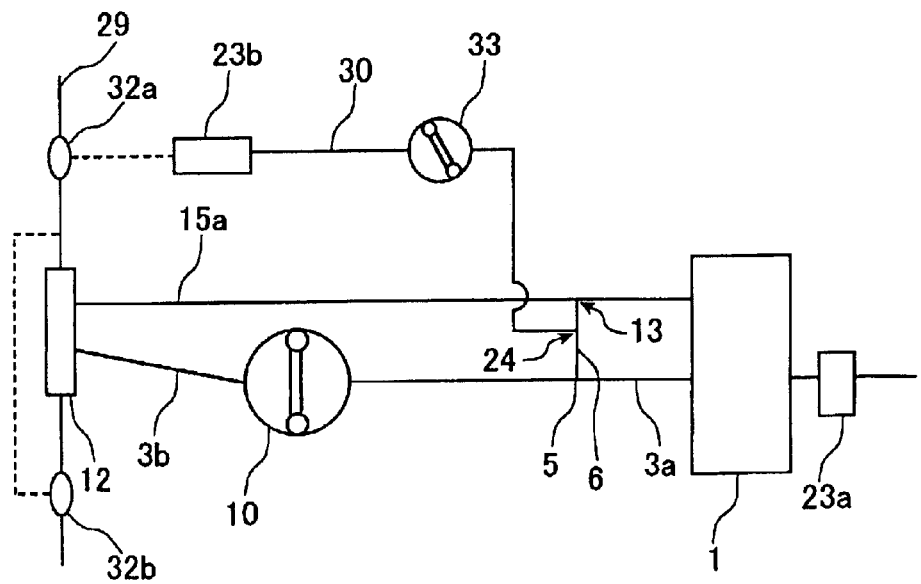
FIG. 8 is a schematic view illustrating another modification of the unit in FIG. 7.

It should be noted that the flow rate adjusting line 27 and the controlling line 35 are not necessarily provided. More specifically, when the dialytic fluid supply/discharge unit 1 is a water removal controlling type, the balance control can be realized. Such a configuration is shown in FIG. 8. The blood circuit connecting line 30 has one end connected to the bypass line 6 branched from the dialytic fluid supply/discharge unit 1 with the ET cut filter 23a, and the other end connected to an A chamber 32a (for an artery). The blood circuit connecting line 30 is provided with the fluid supply pump 33. While the fluid supply rate is adjusted by the fluid supply pump 33, the supplemental fluid is supplied to the A chamber 32a or a V chamber 32b (for a vein), or to both through the ET cut filter 23. The flow rate of dialytic fluid flowing into the dialyzer 12 is adjusted according to the differences in the flow rate between the dialytic fluid supply/discharge unit 1 and the fluid supply pump 33. In view of the balance, the quantity of fluid that is branched and supplied becomes a water removal difference; however, since the same quantity of fluid is supplied into the body, there arises no problem.

In such a case, according to the balance control of the dialytic fluid supply/discharge unit 1, the dialytic fluid removed by the fluid supply pump 33 is of the same quantity as that of water removed from the patient through the dialyzer 12. For instance, while the flow rate of the dialytic fluid of the dialytic fluid supply/discharge unit 1 is increased to 500 ml or more, e.g., 700 ml, the flow rate of the dialytic fluid of the dialytic fluid feed pump 10 is set to be 200 ml/min. Then, the fluid supply rate by the fluid supply pump 33 can be adjusted to be within 0 to 500 ml/min. On the contrary, the flow rate of the dialytic fluid through the dialyzer 12 may be increased, while the fluid supply rate is lowered. As described above, the adjustment can be conducted with ease. In such a manner, the rate can be varied according to the condition of the patient and examination data. For instance, for the patient of a high $\beta_2$-MG and in an unstable circulatory condition, the flow rate of the dialytic fluid is lowered, while the fluid supply rate is increased.

Sixth Embodiment

Figure 9:
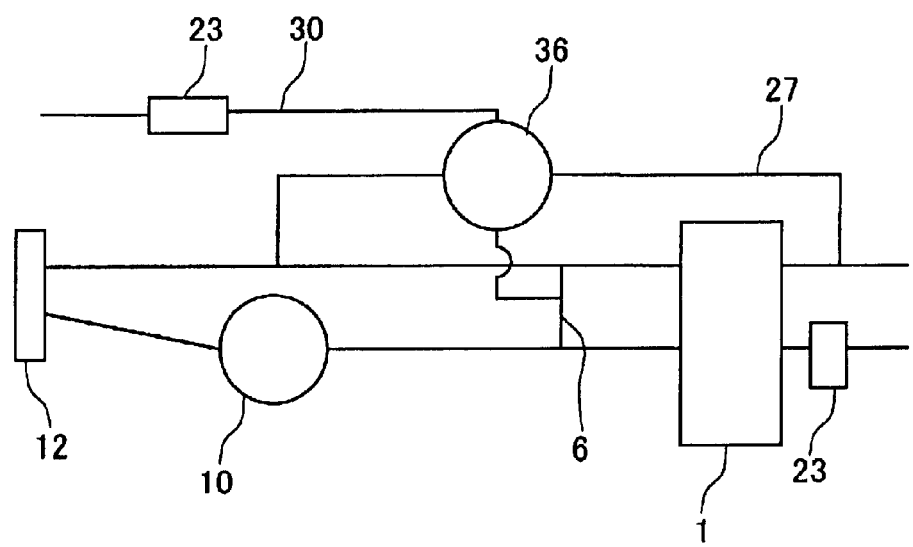
FIG. 9 is a schematic view illustrating a configuration of an essential part of the hemodialyzing unit according to a sixth embodiment of the present invention.
Figure 10:
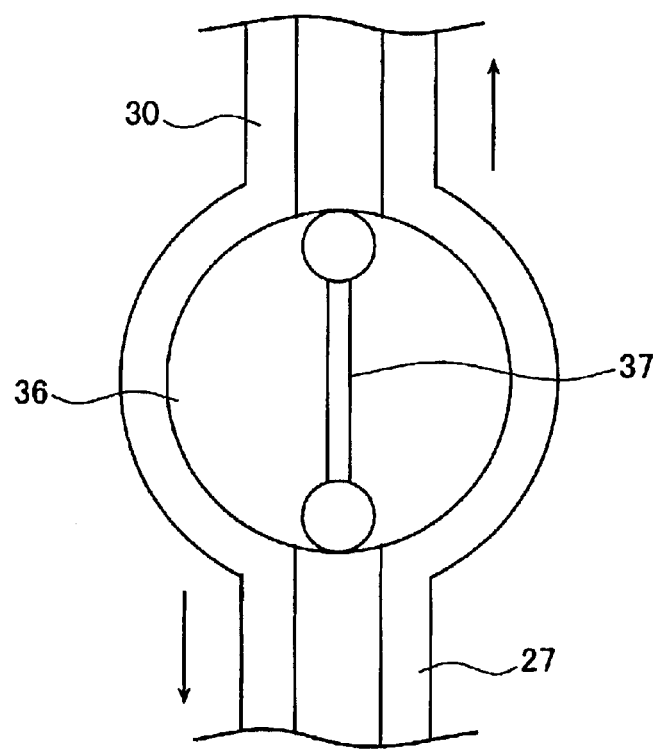
FIG. 10 is an enlarged schematic sectional view illustrating a double pump constituting a dialytic fluid feeding portion in the hemodialyzing unit in FIG. 8.

The hemodialyzing unit in FIG. 7 can be configured so as to obtain three functions of the first flow rate adjusting unit, the second flow rate adjusting unit and the control unit in one unit. The example will be described with reference to FIGS. 9 and 10. In FIG. 9, the common double pump 36 is provided for the flow rate adjusting line 27 and the blood circuit connecting line 30. Then, the two lines are driven by the one pump, to feed fluid. A general configuration of the double pump 36 is shown in FIG. 10. The double pump 36 pressurizes the two different conduits (the flow rate adjusting line 27 and the blood circuit connecting line 30) by the single roller 37, to feed fluid. The double pump 36 can accurately and simply control the dialytic fluid feeding rate through the two lines to become equivalent. The tube having the same diameter is attached to the pump, thereby obtaining the same dialytic fluid feeding rate, while the dialytic fluid feeding direction becomes opposite.

The hemodialyzing units of the present invention described in the above described embodiments can further produce the following effects.

Figure 11:
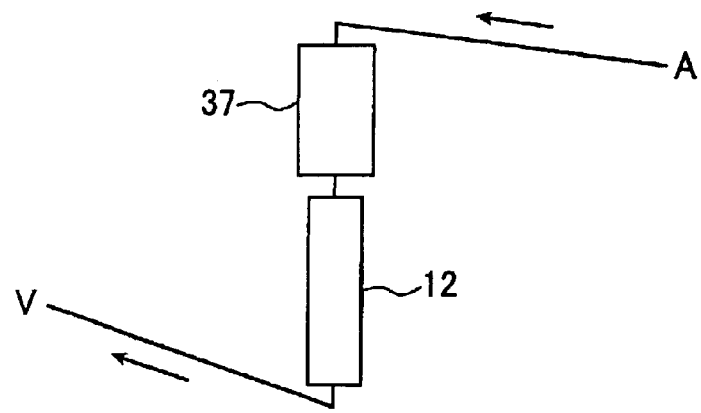
FIG. 11 is a schematic view illustrating a configuration, in which a blood adsorbing column is placed upstream of the hemodialyzer.

For instance, as shown in FIG. 11, the hemodialyzing unit is useful for the case where the HD is conducted at the same time when DHP (Direct Hemo Perfusion) is conducted in a blood circuit in which a blood adsorbing column 37 is placed upstream of the hemodialyzer 12. In the case where the HD also is employed while conducting the DHP for the patient suffering from drug poisoning or the like, the blood flow rate is required to be increased during the DHP so as to remove the drug. On the other hand, regarding the HD, in the case where the patient is in a bad condition or receives the HD for the first time, the HD is required to be conducted with decreasing efficiency. In such a case, if the SHD is conducted with lowering the flow rate of the dialytic fluid, the DHP can be conducted without lowering the blood current.

Moreover, in the case where anticoagulants, even futhan, cannot be used because the patient has a serious bleeding tendency, or when the blood flow rate is decreased, the blood might be coagulated unless the blood flow rate is increased. In such a case, the use of SHD allows the blood current to be increased while the dialytic fluid efficiency is lowered.

As shown in the above two examples, the hemodialyzing unit of the present invention is useful for the case where the blood current is required to be increased, while the dialysis efficiency is required to be lowered.

Moreover, in order to remove $\beta_2$-MG, the dialysis membrane having an enlarged area is effective. However, such a dialysis membrane undesirably causes an increased efficiency in removing low molecular-weight substances such as UN, creatinine, and electrolytes, which results in undesirable increase in the frequency of the occurrence of disequilibrium such as lower blood pressure. In such a case, according to the hemodialyzing unit of the present invention, the disequilibrium can be improved by decreasing the flow rate of the dialytic fluid to a range of 200 to 400 ml/min, while maintaining the removal efficiency of $\beta_2$-MG, so as to suppress the undesirable removal efficiency of low molecular-weight substances. Further, the use of the SHDF allows the adjustment in the fluid supply rate to be facilitated. Therefore, the treatment can be conducted while adjusting each flow rate of the dialytic fluid and the supplemental fluid according to the examination data and the condition of each patient. As described above, not only the blood flow rate but also the flow rate of the dialytic fluid (the flow rate of supplemental fluid in the SHDF) can be adjusted with ease.

As a component co-operated with a Crit-Line or an automatic sphygmomanometer, an SHD (or SHDF) system employing the hemodialyzing unit of the present invention can be added, thereby automatically switching to the SHD (or SHDF) before blood pressure is lowered. In order to co-operate the Crit-Line and the hemodialyzing unit of the present invention, the following configuration is adopted.

Figure 12:
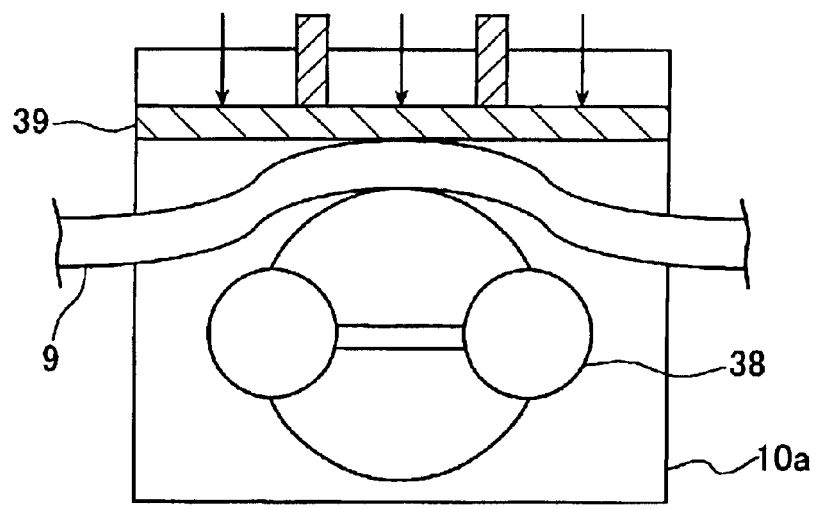
FIG. 12 is a schematic view illustrating a dialytic fluid feed pump having a pump tube that can be freely contacted/discontacted.

As in the hemodialyzing unit in FIG. 6, in the case where the solenoid valve 7 is incorporated into the bypass circuit 6 and the dialytic fluid feed pump 10a for adjusting the dialytic fluid to a low flow rate is attached, the dialytic fluid feed pump 10a in FIG. 12 is employed, for instance. An usual state is different from the state shown in FIG. 12. Although the pump tube 9 is attached to the dialytic fluid feed pump 10a, a roller 38 is not contacted with the pump tube 9, so that the dialytic fluid feed pump 10a cannot function as a pump. Moreover, the solenoid valve 7 is closed. When the Crit-Line detects data showing that a blood pressure might be lowered, the solenoid valve 7 is opened. At the same time, as shown in FIG. 12, a pressurizing plate 39 made of rubber is closely contacted with the roller 38, whereby the roller 38 is in contact with the pump tube 9. As a result, the dialytic fluid feed pump 10a can function as a pump. Accordingly, the dialytic fluid feed pump 10a starts to operate so as to adjust the dialytic fluid to a low flow rate.

In the case where the solenoid valve 7 is incorporated into the bypass line 6, while the pump tube 9 is not contacted with the dialytic fluid feed pump 10a, the following operations should be conducted. When the Crit-Line detects data showing that a blood pressure might be lowered, the solenoid valve is opened, and at the same time, an alarm sound blares. When the solenoid valve is opened, the dialytic fluid passes through the bypass line 6. Therefore, the dialytic fluid does not flow into the dialyzer. Moreover, when the alarm sound blares, the pump tube 9 is manually attached to the dialytic fluid feed pump 10a. Consequently, the pump starts to operate so that the dialytic fluid can be adjusted to a low flow rate. In this state, it may be possible to lower the rate of water removal, or stop the removal. Otherwise, while the pump is not operated and the water removal is stopped, the condition of the patient is kept under observation so as to see if the blood pressure is stabilized. Then, an ECUM may be employed at first, whereby the water removal can be conducted although the dialytic fluid passes through the bypass line, and then the dialytic fluid is adjusted to a low flow rate, gradually.

EXAMPLE

An example of the hemodialyzing unit configured as in FIG. 1 will be described. When the flow rate of dialytic fluid in the dialytic fluid supply/discharge unit 1 is set to be 300 ml/min (18,000 ml/hr), 300 ml/min of dialytic fluid passes through the upstream supply line 3a. When it is desired to feed 50 ml/min of dialytic fluid to the dialyzer 12, the flow rate is adjusted to be 50 ml/min by the dialytic fluid feed pump 10. The dialytic fluid that is not fed to the dialyzer 12 passes through the bypass line 6 at a flow rate of 250 ml/min. Then, 50 ml/min of the dialytic fluid that passes through the dialyzer 12 and 250 ml/min of the dialytic fluid that passes through the bypass line are merged at the dialytic fluid discharge line coupling portion 13, to flow to the downstream discharge line 15b.

In such a manner, the patient in a bad condition was transferred from an ICU (Intensive Care Unit) to a general treatment of the general dialysis. For example, the CHDF was tested to a certain patient in a bad condition at the ICU employing the device for the exclusive use of the CHDF and a supplemental fluid for a filtration-type artificial kidney. Since his/her condition was slightly stabilized, he/she was transferred from the ICU to a Kidney Center where the general hemodialysis was conducted, to try the general dialysis treatment, which was not possible. Then, the unit of the present invention was employed. According to the above-described method, the dialytic fluid was set at a low flow rate at first, and then the flow rate was gradually increased from the dialysis of high sodium at a low flow rate (from the flow rate of 3000 ml/hr to 6000 ml/min). Finally, the general dialysis could be conducted to the patient (the $45^{th}$ Japanese Society for Dialysis Therapy, page 609).

According to the present invention, the following effects can be obtained.

(1) Since the unit or circuit for the exclusive use is not required, the configuration is simplified, thereby facilitating the operations and saving the preparation time. Further, the CHD or CHDF treatment can be conducted at low cost.

(2) The device of the present invention can be configured so that the treatments can be switched between the general hemodialysis and the CHD or CHDF treatment. Even in the case of switching, complicated operations and methods for switching are not required. Therefore, for the patient who cannot receive the hemodialysis at first, the treatment can be shifted from the CHD or CHDF treatment to the general dialysis. Moreover, the treatment is adjusted according to the condition of the patient (blood pressure or the like).

(3) By adding the valve to the basic configuration, in the case where the feeding function of the dialytic fluid supply/discharge unit falls into an abnormal condition, the valve is closed so that a recirculating loop can be formed in which the dialytic fluid circulates without passing through the dialytic fluid supply/discharge unit. Accordingly, the safety of the patient can be secured.

(4) The flow rate of dialytic fluid passing through the dialyzer can be controlled irrespective of the flow rate of dialytic fluid supply/discharge unit.

(5) The CHD or CHDF can be conducted employing a dialytic fluid, thereby facilitating a fluid prescription that cannot be conducted easily by a supplemental fluid for a filtration-type artificial kidney. For instance, if the dialytic fluid supply/discharge unit provided with a unit for injecting sodium is employed, the dialysis of high sodium can be conducted. Further, the preparation and adjustment for the supplemental fluid can be simplified and shortened.

(6) An additional simple component used with the basic configuration enables the on-line CHDF wherein the balance can be kept automatically between the quantity of fluid removed from blood and the flow rate of supplemental fluid from the dialytic fluid side to the blood side.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A hemodialyzing unit comprising a dialytic fluid supply line for feeding a dialytic fluid from a dialytic fluid supply/discharge unit to a dialyzer, a dialytic fluid discharge line for feeding a dialytic fluid discharged from the dialyzer to the dialytic fluid supply/discharge unit, and a bypass line for connecting both the lines at an intermediate portion of each, wherein the dialytic fluid supply line includes an upstream supply line extending from the dialytic fluid supply/discharge unit to a coupling portion to the bypass line and a downstream supply line extending from the coupling portion to the bypass line to the dialyzer, the dialytic fluid discharge Line includes an upstream discharge line extending from the dialyzer to the coupling portion to the bypass line and a downstream discharge line extending from the coupling portion to the bypass line to the dialytic fluid supply/discharge unit, a flow rate adjusting member is provided from the downstream supply line, and complementary connector pairs are provided for the upstream supply line, the downstream discharge line, the downstream supply line extending from an attachment portion of the flow rate adjustment member to the dialyzer and the upstream discharge line, respectively, whereby the respective lines are capable of being disconnected/reconnected at the complementary connector pair.

2. The hemodialyzing unit according to claim 1, wherein the flow rate adjusting member is a dialytic fluid feed pump capable of adjusting a flow into of dialytic fluid in a lower flow rate range than the dialytic fluid supply/discharge unit.

3. The hemodialyzing unit according to claim 1, wherein a dialytic fluid feeding rate through the upstream supply line is larger than that through the downstream supply line.

4. The hemodialyzing unit according to claim 2, wherein the dialytic fluid feed pump is capable of adjusting the flow rate to be 150 ml/hr.

5. The hemodialyzing unit according to claim 2, wherein the dialytic fluid feed pump is capable of adjusting the flow rate in a range of 150 ml/hr to 3000 ml/hr, at least.

6. The hemodialyzing unit according to claim 1, wherein at least one open/close member is provided for the upstream supply line and the downstream discharge line, respectively.

7. The hemodialyzing unit according to claim 1, wherein an open/close member is provided for the bypass line.

8. The hemodialyzing unit according to claim 1, wherein each of the complementary connector pairs is a lure connector or a lock connector having a combination of a male connector and a female connector.

9. The hemodialyzing unit according to claim 1, wherein at least one open/close member is provided for the upstream supply line and the downstream discharge line, respectively, the upstream supply line is provided with the complementary connector pair on the upstream of the open/close member provided on the line and the downstream discharge line is provided with the complementary connector pair on the downstream of the open/close member provided on the line.

10. A hemodialyzing circuit comprising:

a circuit body including a dialytic fluid supply line for feeding a dialytic fluid from a dialytic fluid supply/discharge unit to a dialyzer and a dialytic fluid discharge line for feeding a dialytic fluid discharged from the dialyzer to the dialytic fluid supply/discharge unit, wherein the dialytic fluid supply line has a first detachable portion composed of a complementary connector pair at the intermediate portion so as to be disconnected/reconnected at the first detachable portion by detachment of the complementary connector pair at the first detachable portion, and the dialytic fluid discharge line has a second detachable portion composed of a complementary connector pair at the intermediate portion so as to be disconnected/reconnected at the second detachable portion by detachment of the complementary connector pair at the second detachable portion; and an incorporation dialytic fluid circuit including a dialytic fluid supply extension-line, a dialytic fluid discharge extension-line, and a bypass line for connecting both the extension lines at an intermediate portion of each, complementary connectors being disposed at both the ends of the dialytic fluid supply extension-line so as to be connected to each of disconnected complementary connectors of the first detachable portion, complementary connectors being disposed at both the ends of the dialytic fluid discharge extension-line so as to be connected to each of disconnected complementary connectors of the second detachable portion, and a flow rate adjusting member being provided between a coupling portion to the bypass line of the dialytic fluid supply extension-line and one end of the dialytic fluid supply extension-line, wherein the incorporation circuit is detachable provided between disconnected ends of the circuit body at the respective first and second detachable portions.

11. An incorporation dialytic fluid circuit comprising a dialytic fluid supply extension-line, a dialytic fluid discharge extension-line, and a bypass line for connection both the extension lines at each intermediate portion, wherein the dialytic fluid supply extension-line is provided with complementary connectors at both the ends thereof, the dialytic fluid discharge extension-line is provided with complementary connectors at both the ends thereof, and at least a part of a component constituting a flow rate adjusting member is provided between a coupling portion to the bypass line of the dialytic fluid supply extension-line and one end of the dialytic fluid supply extension-line.

12. The hemodialyzing unit according to claim 1 comprising a flow rate adjusting line including a first flow rate adjusting unit for adjusting a flow rate of dialytic fluid and arranged in parallel to the dialytic fluid discharge line, a blood circuit connecting line including a second flow rate adjusting unit for adjusting a flow rate of dialytic fluid and arranged so as to connect the bypass line to the blood circuit, and a control unit for controlling the first end second flow rate adjusting units so that a flow rate of dialytic fluid through the flow rate adjusting line is equal to that through the blood circuit connecting line.

13. The hemodialyzing unit according to claim 12, wherein the first flow rate adjusting unit, the second flow rate adjusting unit, and the control unit are constituted as a single unit.

14. The hemodialyzing unit according to claim 13, wherein the single unit is composed of a double pump that pressurizes two different conduits by a common roller for feeding fluid.

15. The hemodialyzing unit according to claim 12, wherein the control unit is operated according to a weight balance control or a volume control.

* * * * *